US012672908B2

(12) United States Patent
Götz et al.

(10) Patent No.: US 12,672,908 B2
(45) Date of Patent: Jul. 7, 2026

(54) MONITORING UNIT AND HIGH FREQUENCY SURGERY SYSTEM HAVING SUCH A MONITORING UNIT

(71) Applicant: COCO BETEILIGUNGSGESELLSCHAFT MBH, Sonthofen (DE)

(72) Inventors: Stefan Götz, Forstern (DE); Pascal Albert Scherz, Munich (DE); Robert Ludwig Conle, Sonthofen (DE)

(73) Assignee: Forbencap GmbH, Sonthofen (DE)

( * ) Notice: Subject to any disclaimer, the term of this patent is extended or adjusted under 35 U.S.C. 154(b) by 537 days.

(21) Appl. No.: 18/009,613

(22) PCT Filed: Jun. 9, 2021

(86) PCT No.: PCT/EP2021/065506
§ 371 (c)(1),
(2) Date: Dec. 9, 2022

(87) PCT Pub. No.: WO2021/250116
PCT Pub. Date: Dec. 16, 2021

(65) Prior Publication Data
US 2023/0218333 A1 Jul. 13, 2023

(30) Foreign Application Priority Data

Jun. 12, 2020 (DE) ..................... 10 2020 003 524.8

(51) Int. Cl.
*A61B 18/14* (2006.01)
*A61B 18/12* (2006.01)
(Continued)

(52) U.S. Cl.
CPC .......... *A61B 18/14* (2013.01); *A61B 18/1206* (2013.01); *A61B 2017/00199* (2013.01);
(Continued)

(58) Field of Classification Search
CPC . A61B 18/1206; A61B 18/1244; A61B 18/14; A61B 18/16; A61B 2018/00577;
(Continued)

(56) References Cited

U.S. PATENT DOCUMENTS 6,083,221 A * 7/2000 Fleenor .................. A61B 18/16
607/152
6,339,722 B1 * 1/2002 Heethaar .............. A61B 5/0537
600/547
(Continued)

FOREIGN PATENT DOCUMENTS

DE 42 32 255 2/1994
DE 11 2013 001 594 10/2019
(Continued)

OTHER PUBLICATIONS

European Patent Office, International Search Report, Sep. 22, 2021.
(Continued)

*Primary Examiner* — Michael F Peffley
(74) *Attorney, Agent, or Firm* — Warren D. Schickli; Stites & Harbison PLLC

(57) ABSTRACT

A monitoring unit which is configured to monitor a patient during an operation of a high-frequency surgery device, wherein the high-frequency surgery device is configured to separate and/or coagulate biological tissue by means of high-frequency electrical energy, wherein the monitoring unit has: measuring electrodes which are disposed in a periphery of the patient, and an evaluation and control unit which is configured to impress a predetermined measuring alternating voltage or a predetermined measuring alternating current on the measuring electrodes, and to monitor an impedance decreasing between the measuring electrodes and to monitor a time curve of the impedance and/or to monitor a temporal change thereof.

20 Claims, 5 Drawing Sheets

(51) Int. Cl.
   *A61B 17/00*        (2006.01)
   *A61B 18/00*        (2006.01)
(52) U.S. Cl.
   CPC ............... *A61B 2018/00589* (2013.01); *A61B 2018/00791* (2013.01); *A61B 2018/00845* (2013.01); *A61B 2018/00869* (2013.01); *A61B 2018/00875* (2013.01); *A61B 2018/00892* (2013.01); *A61B 2018/00898* (2013.01)
(58) Field of Classification Search
   CPC .......... A61B 2018/00589; A61B 2018/00601; A61B 2018/00607; A61B 2018/00666; A61B 2018/00791; A61B 2018/00845; A61B 2018/00869; A61B 2018/00875; A61B 2018/00892; A61B 2018/00898; A61B 2018/165; A61B 2018/167; A61B 2560/0266; A61B 2560/0468; A61B 2562/0271; A61B 5/01; A61B 5/053; A61B 5/4848; A61B 5/6892; A61B 5/746
   See application file for complete search history.

(56)                References Cited

U.S. PATENT DOCUMENTS

| | | | |
|---|---|---|---|
| 7,837,680 B2 | 11/2010 | Isaacson et al. | |
| 8,821,487 B2 | 9/2014 | Arts et al. | |
| 8,864,756 B2 * | 10/2014 | Strauss | A61B 18/1233 606/35 |
| 9,867,650 B2 | 1/2018 | Ehninger et al. | |
| 10,085,791 B2 * | 10/2018 | Ehninger | A61B 18/1233 |
| 10,646,266 B2 | 5/2020 | Smith et al. | |
| 2008/0051777 A1 | 2/2008 | Haemmerich | |
| 2008/0281309 A1 * | 11/2008 | Dunning | A61B 18/16 606/32 |
| 2009/0234352 A1 * | 9/2009 | Behnke | A61B 18/16 606/35 |
| 2015/0320478 A1 * | 11/2015 | Cosman, Jr. | A61B 18/16 606/34 |
| 2015/0320481 A1 | 11/2015 | Cosman, Jr. et al. | |

FOREIGN PATENT DOCUMENTS

| | | |
|---|---|---|
| DE | 10 2018 114 482 | 12/2019 |
| EP | 1759651 | 8/2009 |
| WO | 2021250116 | 12/2021 |

OTHER PUBLICATIONS

Machine Translation of WO 2021250116, Google Patents.
Machine Translation of DE 42 32 255 C1, Google Patents.
Machine Translation of DE 10 2018 11 482 A1, Google Patents.
Machine Translation of DE 11 2013 001 594 B4, Google Patents.

* cited by examiner

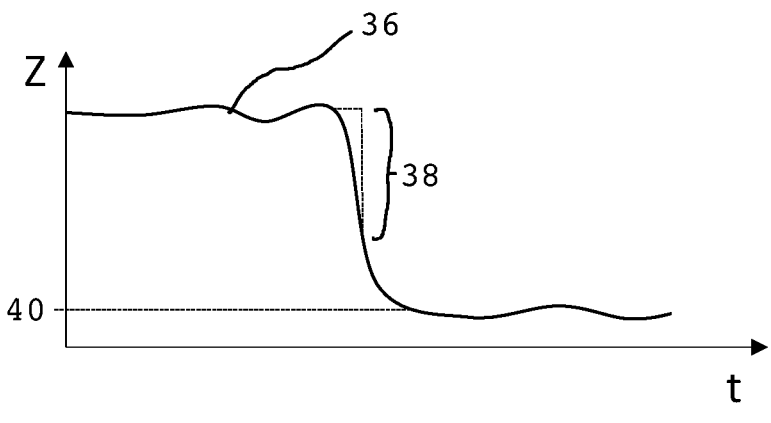
FIG. 3
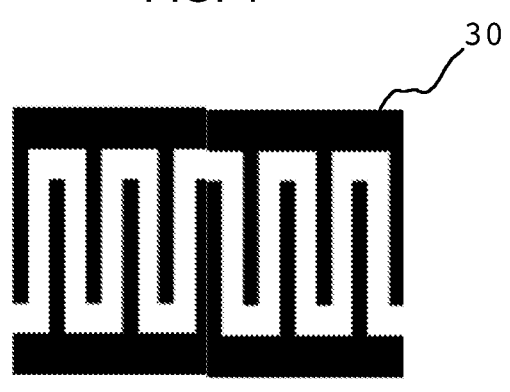
FIG. 4
FIG. 5

MONITORING UNIT AND HIGH FREQUENCY SURGERY SYSTEM HAVING SUCH A MONITORING UNIT

This National Stage application claims priority to International Patent Application No. PCT/EP2021/065506, filed Jun. 9, 2021, the entirety of the contents of which is incorporated by reference herein, which claims priority to German Patent Application No. 10 2020 003 524.8, filed Jun. 12, 2020.

FIELD OF THE INVENTION

The present invention relates to a monitoring unit which is configured to monitor a patient during operation of a high-frequency surgery device and to a high-frequency surgery system having such a monitoring unit.

BACKGROUND OF THE INVENTION

High-frequency surgery (short: HF surgery) has become a dominant type of electrosurgery. It comprises using electrical energy (as assistance) for effecting a (specific) thermally induced change and/or destruction of tissue cells in order to achieve what is known as hemostasis (stopping bleeding), a separation of tissue and/or a sealing of tissue (coagulation). High-frequency alternating current (for example, 0.3 to 4 MHz) is conducted into the tissue to be treated via electrodes (or applicators). In the tissue, a thermal tissue interaction occurs due to an electrical tissue resistance present in the tissue which will be explained in further detail below.

A substantial advantage of separating tissue using high-frequency surgery compared to conventional surgical cutting techniques, for example by means of a scalpel or scissor, is that a bleeding can be stopped at the same time as the cut by sealing the affected blood vessels. Other advantages of HF surgery technology include, but are not limited to, prevention of a transmission of germs, mechanical tissue conservation and the possibility for endoscopic use.

Based on the advantages for the patient and the surgeon and the steadily increasing demand from different medical fields, the need for HF surgical technologies and their continued development is in the focus of medical technology and establishes an indisputably versatile commercial applicability for this technology.

From an electrotechnical point of view, what is known as electric current density (physical unit: ampere per cm²) can be assigned a key role in HF surgery technology, the electric current density colloquially characterizing how densely packed an electric current flows. For example, electric current density also characterizes the load of an electrical conductor (in the case of HF surgery represented by animal tissue or human tissue) caused by an (alternating) electric current. Electric current density is defined as the ratio of current intensity I to a cross-sectional area A available to the current.

In HF surgery, a (desired) cutting and/or coagulation effect (coagulation=precipitation, flocculation or clotting of a substance) can only be achieved for the treated tissue if the electric current density in the tissue section treated by means of the high-frequency technology is large enough (usually between 1 to 6 ampere per cm²). The electric current density is inversely proportional to the square of a distancer from the application center ($J\sim1/r^2$). On the contrary, assuming homogeneous tissue properties, a (measurable) temperature increase decreases according to the fourth power of the distancer from the application center ($\Delta T\sim1/r^4$).

When cutting tissue by means of high-frequency alternating current, locally restricted high electric current densities can be generated in the tissue (section) to be cut, preferably via small-area knife-shaped or needle-shaped electrodes. The tissue treated using the high-frequency alternating current thus heats up to over 100° C. in a flash, such that a resulting steam pressure explosively ruptures the cell membranes of the tissue cells. The produced electrically insulating steam between electrode and tissue thus prevents unimpeded ohmic current flow into the tissue, such that a voltage (so-called cutting voltage) builds up between electrode and tissue, through which a spark formation between electrode and tissue is produced. A further energy input takes place via sparks. Extremely high energy densities occur in the roots of the sparks, which are only a few μm in size ($r_F$=10 to 20 μm), under the influence of which the involved tissue cells evaporate. It does not matter whether the process takes place openly under environmental conditions, in a protective atmosphere or in an electrically non-conductive liquid.

The effect of an HF current in the treated tissue is mainly determined by its exposure time, voltage level and the degree of amplitude modulation. The frequency (0.3 to 5 MHz), on the other hand, is not a decisive factor. An important characteristic variable is what is known as the crest factor (or crest). It describes the ratio of peak value (crest value) to RMS value of an alternating electrical quantity and gives an indication of how strongly a current is modulated in its amplitude. For example, a sinusoidal alternating voltage with a RMS value ($U_{eff}$) of 230 $V_{eff}$ (mains voltage) has a peak value ($U_p$) of approx. 325 $V_p$, so that the crest factor ($C_F$) is 1.41 ($\sqrt{2}$) in this case. Accordingly, at constant output power, the output voltage must also be greater for a current with a high crest factor.

The core part of HF surgery technology is what is known as a high-frequency generator, although the underlying technology has improved steadily over the past decades driven by manifold microprocessor and control technology developments. In modern high-frequency generators, a mains currents supplied to the generator is converted to a high-frequency current (necessary for HF surgery). Driven by safety-related standardization and technical advancements (e.g., by standardization (IEC 60601-2-2)), the high-frequency output power of HF surgical equipment is continuously reduced, and is limited to an upper limit of 400 W. Furthermore, IEC 60601-2-2 recommends using operating frequencies above 300 kHz and below 5 MHz.

In the wake of safety-motivated standardization, modern high frequency generators continue to feature a majority of internal monitoring devices, such as dispersive electrode monitoring, overdose protection circuits, visual and audible activation indicators, and what is known as HF leakage current compensation, whereby a higher degree of security for the patient and the surgeon can be guaranteed during use.

Despite the advantages described above and continuous (safety-related) technical developments, the problem of (sometimes severe) burns and/or chemical burns of the patient in tissue areas that are often at a distance from the actual application center of the HF surgery device (i.e., the operating environment), for example, on the feet, hands, parts of the upper and lower back, etc., still exists in HF surgery applications. These burns and/or chemical burns (in case of additional interaction with disinfectant) can be attributed to side effects of an energy input of a high-frequency electrical energy in the tissue of the patient, which will be described in more detail below.

A potential "source" for unwanted burns and/or chemical burns is often improper handling of the pre-surgical preparation of the patient, e.g., improper positioning (or placement) of the patient on an operating table or chair. Although attempts are made to counteract this incorrect operation or incorrect handling (human error) by defining and standardizing a large number of safety-relevant rules of application, which may be successful depending on the operating environment, the occurrence of burns and chemical burns to the patient is not completely prevented.

Unwanted patient injuries on tissue sections not involved in the surgery often cause indemnity claims (for example, in the form of compensation for personal suffering and the reimbursement of medical expenses) afterwards, in some cases to a not inconsiderable extent, which must be cushioned or compensated for by the hospital operator by taking out an appropriate insurance cover (and the associated additional expenses) or by raising equity capital.

The physical cause of burns or chemical burns on tissue parts, which are often at a distance from the actual surgical procedure, can be attributed, for example, to a patient's position that is not completely electrically insulated and the associated unwanted and uncontrolled discharge of currents (along the path of least resistance). Furthermore, in the event of (accidental) contact between a part of the patient's tissue (e.g., a foot) and equipment (tubes, etc.) in the patient's periphery, an unanticipated conductivity bridge may be created through which the current introduced by the HF surgery device can be (additionally) discharged. These conductivity bridges can also occur on materials which are electrically insulating in the low frequency range and are usually due to capacitive coupling effects. Thus, for example, the user expects a plastic hose to have an electrically insulating effect, although the same plastic hose is electrically conductive when it comes into contact with high-frequency electrical energy.

The degree of occurrence of unwanted burns and/or chemical burns of the patient also differs depending on the HF technology used, with a distinction being made between monopolar and bipolar application. For further information, reference is made to Kramme, Rüdiger, ed. Medizintechnik: Verfahren-Systeme-Informationsverarbeitung [*EN: Medical engineering: methods—systems—information processing*]. Springer-Verlag, 2016, Chapter 32.

Monopolar HF surgery technology features an active electrode and a dispersive surface electrode, which are each connected to the HF generator. On the active electrode, the physical effects (cutting, coagulating) required for HF surgery are generated. The dispersive electrode, which is larger compared to the active electrode, is placed on an upper leg or upper arm of the patient, for example. A contact area between the dispersive electrode and the skin (surface) of the patient is preferably as large as possible in this case (=electric current density as low as possible). The high-frequency alternating current introduced by the active electrode is ideally fully discharged via the neutral electrode. However, the rest of the patient's body is ideally stored so as to be electrically insulated.

With bipolar HF surgery technology, on the other hand, both the active and the dispersive electrode are integrated in one instrument, for example bipolar forceps with insulated branches. With this technology, the high-frequency alternating current flows into the tissue via the active electrode and back to the HF generator via the dispersive electrode. This means that the alternating current flows in a narrowly circumscribed tissue area between the two electrode tips, which is why the bipolar technology ensures a higher degree of safety compared to the monopolar technology, especially for delicate neurological dissections. Additionally, compared to the monopolar technology, the risk of unwanted burns and/or chemical burns on the patient, for example because of touching conductive items during surgery, is rather low, but not excluded.

SUMMARY OF THE INVENTION

In light of the foregoing, it is an object of the present invention to provide a monitoring technology by means of which a number of unwanted burns and/or chemical burns on tissue areas which are not involved in the actual surgical procedure can be decreased.

According to a first aspect of the invention, this object is attained by a monitoring unit which is configured to monitor a patient during an operation of a high-frequency surgery device. The high-frequency surgery device is configured to separate and/or coagulate biological tissue (of the patient) by means of high-frequency electrical energy. The monitoring unit according to the invention has measuring electrodes which are disposed in a periphery of the patient, and an evaluation and control unit, which is configured to impress a predetermined measuring alternating voltage or a predetermined measuring alternating current on the measuring electrodes, and to monitor an impedance decreasing between the measuring electrodes, and to monitor a time curve of the impedance and/or to monitor a temporal change thereof. Preferably, the evaluation and control unit is configured to generate a warning signal if a relative change in impedance in the time curve of the impedance undercuts or exceeds a predetermined first limit value and/or the impedance undercuts a predetermined second limit value.

The monitoring unit according to the invention is advantageous in that by means of the impedance measurement and monitoring the periphery of the patient, they can be protected from unwanted burns and/or chemical burns (produced for example because of uncontrolled discharge currents and/or leakage currents) on tissue parts (for example on a foot, a hand and/or on parts of the patient's back) which are not actually involved in the surgical procedure.

The impedance measurement allows a prediction of an impending burn and/or chemical burn, so to speak, which can be pointed out by generating the warning signal, such that, for example, the surgeon or ancillary staff can intervene manually. Alternatively or additionally, the high-frequency surgery device can be shut off in a controlled manner by means of the evaluation and control unit or by means of a high-frequency generator.

The high-frequency surgery device preferably has an active electrode and a dispersive electrode, wherein at least the active electrode is connected to a preferably available high-frequency generator. The active electrode is configured to separate and/or coagulate biological tissue by means of the high-frequency electrical energy, and the dispersive electrode is configured to discharge the high-frequency electrical energy from the biological tissue. Preferably, the dispersive electrode is also connected to the high-frequency generator.

An uncontrolled high-frequency current flow via a tissue section or a tissue part in the periphery of the surgical zone can be produced, for example, by an improper positioning of the patient on the surgical table. For example, by an (accidental) contact of surgical equipment which is conductive in the high-frequency range (breathing hose or aspirator hose, parts of the operating table), what is known as a conductivity bridge can be caused, via which the introduced alternating current introduced via the active electrode can flow off at least partly or (in the worst case) fully. Ideally, the cutting current introduced via the active electrode should flow off solely via the dispersive electrode. By means of the impedance measurement according to the invention, these conductivity bridges can be detected practically in real time by means of the impedance measurement according to the invention.

The wording "in a periphery of the patient" means that the measuring electrodes (preferably a plurality of measuring electrodes, but at least more than one measuring electrode) are disposed in the immediate and/or indirect surroundings of the center of the operation and/or on or around the patient. In other words, this means that the measuring electrodes can be disposed, for example, on a surgical table on which the patient is positioned during the surgery, for example so as to be distributed (regularly) over a contact surface (preferably entirely).

Alternatively or additionally, the measuring electrodes can be disposed on surgical equipment (breathing hoses and aspirator hoses, wiring, etc.) in the periphery of the patient. Preferably, the measuring electrodes are disposed on surfaces which are in direct contact with a body part or the skin of the patient (for example the back area by directly positioning it on the operating table) and/or which can potentially come into contact with a tissue section (or a body part) of the patient (for example, in case of an improper positioning, the hand of the patient sliding off the operating table and the hand subsequently coming into contact with a breathing hose, for example).

Additionally, situations may arise in which electrically conductive (bodily) fluid(s) (blood, excrements, etc.) leak out uncontrolledly and, when they come into contact with material surfaces, such as the surgical table or operating table, abruptly increase the conductivity between these materials and the skin lying on them, thus creating conductivity bridges at these points.

If there is an unexpected or uncontrolled current flow over a conductivity bridge, an impedance measured on the measuring electrodes in a passive state (i.e., when current is discharged fully via the dispersive electrode without a current flow over an additional conductivity bridge) abruptly decreases (impedance $|Z|=U_{eff}/I_{eff}$). If the relative change of the impedance exceeds or undercuts the predetermined first limit value (which has been determined by means of a plurality of test measurements, for example) and/or if the impedance undercuts a predetermined second limit value (for example, an impedance so low that an immediate burn of the respective tissue must be expected), in the measured curve of the impedance, the warning signal is preferably generated subsequently and/or the evaluation and control unit causes the high-frequency surgery device to shut off.

The wording "relative change of the impedance" means a respective gradient (increase or decrease) of the impedance over time. The evaluation and control unit is configured to determine the gradient from the time curve of the impedance ($\nabla f = \partial Z/\partial t$, with Z=impedance [$\Omega$] and t=time [s]).

Preferably, the measuring electrodes are configured such that they jointly act as the dispersive electrodes.

In the present case, "measuring alternating voltage" or "measuring alternating current" means the current or the voltage introduced to the measuring electrodes for impedance measurement. Between the measuring electrodes, a preferably continuous impedance measurement can be carried out, i.e., for example, a measuring alternating current is impressed and a voltage is measured or a measuring alternating voltage is impressed and a corresponding current is measured. If the impedance between two measuring electrodes each either decreases considerably ($\partial Z/\partial t$) (first limit value) or decreases to below a threshold (second limit value), this suggests a leakage of conductive fluids or that an electroconductive object touches a skin area and permits a response.

It should also be mentioned that the variety of different types of tissue (including muscle, fat, etc.) and their conditions (bleeding, dry, close or loose electrode contact, etc.) to which a high-frequency (cutting) current is applied or over which a high-frequency current is discharged represent a broad impedance spectrum (approx. 50-1000$\Omega$).

The impedance measurement by means of the measuring electrodes according to the invention is fundamentally differentiated, in particular, from existing safety devices, such as dispersive electrode monitoring, overdose protection circuits, optical and acoustic activation indicators and HF leakage current compensation, all of which may be integrated in a high-frequency generator. The differentiation is based in particular in the fact that the monitoring device according to the invention is preferably decoupled from the safety concepts of the high-frequency generator as an independent or separate monitoring and/or safety unit. In this way, potential danger spots for looming burns can be identified preferably over the entire contact surface of the patient's body and eliminated at an early stage, e.g., by means of a warning signal. This means that faults caused by human error can also be monitored, which is not possible or only possible to a limited extent with the safety systems integrated in the high-frequency generator.

Furthermore, according to a second aspect of the invention. The object is attained by a monitoring unit which is configured to monitor a patient during an operation of a high-frequency surgery device, wherein the high-frequency surgery device is configured to separate and/or coagulate biological tissue (of the patient) by means of high-frequency energy. The monitoring unit according to the second aspect has measuring sensors and an evaluation and control unit, wherein the measuring sensors are configured to detect a parameter which is produced during the separation and/or coagulation of the biological tissue because of the high-frequency energy. Preferably, the evaluation and control unit is configured to generate a warning signal based on the parameter.

In this aspect, the measurement or the detection of an unintended and/or uncontrolled current flow over a part of the patient's body, some of which may cause severe burns and/or chemical burns, is performed using measuring sensors, i.e., not directly by measuring impedance values. Rather, it is possible to also monitor looming burns and/or chemical burns by means of further technical procedures, if possible over the entire body surface of the patient, and to detect looming burns at an early stage. Depending on the physical measuring principle (e.g., via a temperature measuring sensor, etc.), the evaluation and control unit records a parameter on the basis of which it is possible to indirectly conclude that an unwanted current is flowing through a part of the patient's body.

According to a third aspect, the object is attained by a high-frequency surgery system which has a high-frequency generator which is configured to generate a high-frequency energy. Furthermore, the system according to the invention has a high-frequency surgery device having an active electrode and a dispersive electrode, wherein at least the active electrode is connected to the high-frequency generator. The active electrode is configured to separate and/or coagulate biological tissue by means of the high-frequency electrical energy and the dispersive electrode is configured to discharge the high-frequency electrical energy from the biological tissue. Furthermore, the high-frequency surgery system according to the invention has an embodiment of the monitoring unit according to the invention.

Furthermore, according to the first or second aspect, it is advantageous to couple the monitoring unit according to the invention with one or several optical sensors (e.g., cameras), for example, in order to obtain a live image of the surgery process. The (3D) images captured by the camera(s) can preferably be overlaid with the measured quantities (impedance or parameter) in such a way that a visual localization of the unwanted current flow or the location where an (additional) current bridge occurs is possible by means of a display, for example.

An advantage of the first and second aspect is that a simple retrofit is possible, such that all existing systems can be retrofitted regarding their safety technology. It is also advantageous that a significantly higher level of safety for the surgeon and in particular for the patient can be achieved by the monitoring system according to the invention. Misconduct or a disregard of regulations during the preparation of the surgery, e.g., with the positioning of the patient, can thus be at least partially compensated for by the monitoring unit according to the invention. This results in fewer burns and a reduction in the burden on insurers, and thus in direct and indirect cost savings.

The high-frequency surgery device is preferably a high-frequency electric scalpel. The high-frequency surgery device can have a monopolar or bipolar design. Furthermore, the high-frequency surgery device can generally be a device which applies high-frequency electrical energy for surgical purposes.

In an embodiment, the measuring electrodes are disposed on several components in the periphery of the patient, such that the evaluation and control unit is configured to determine a spatial impedance distribution in the periphery of the patient.

An advantage of this embodiment is that all equipment located in the vicinity of the patient or the patient's body can be monitored for the potential formation of a conductivity bridge or current bridge. Thus, it is possible to indirectly monitor preferably all the patient's body parts that are susceptible to burns by taking impedance measurements on preferably all the components in the surgical area.

In another embodiment, the monitoring unit further has a display and the evaluation and control unit is configured to display the preferred warning signal in the form of a spatial position and location of a place in the periphery of the patient at which the first limit value is exceeded or undercut and/or the second limit value is undercut on the display.

This embodiment is advantageous in that it allows the surgeon or ancillary staff to locate as accurately as possible the location of the uncontrolled current leakage that is not via the dispersive electrode provided for this purpose. Thus, a targeted intervention is possible and a looming burn can be prevented or at least stopped at an early stage so that collateral damage to the affected skin tissue can be prevented.

In another embodiment, the evaluation and control unit is further configured to shut off the high-frequency surgery device when the value exceeds or undercuts the first limit value and/or when the value undercuts the second limit value.

This embodiment is advantageous in that the surgeon or ancillary staff is/are not required to intervene manually if an additional conductivity bridge is detected, but instead, the high-frequency surgery device is shut of automatically in order to prevent burns. A shut-off causes the current flow through the active electrode and thus the introduction of high-frequency electrical energy to stop abruptly, so that burns do not occur.

It should be mentioned that the mechanism for shutting off can preferably be shut off manually, as situations can repeatedly arise, in particular during emergency operations, in which electroconductive (bodily) fluid(s) (blood, excrements, etc.) can leak out uncontrolledly and, when they come into contact with material surfaces, such as the surgical table or operating table, abruptly increase the conductivity between these materials and the skin lying on them, thus generating conductivity bridges. Despite the fact that this causes unwanted burns, in these exceptional situations it is more crucial to ensure an operation of the high-frequency surgery device because of the acute danger to human life.

In another embodiment, the measuring electrodes form a pattern of surface electrodes which are spatially distributed, adjacent and preferably electrically insulated from each other and the evaluation and control unit is configured measure the impedance between each two adjacent surface electrodes.

This embodiment is advantageous in that, it is possible to localize (as accurately as possible) the area where a conductivity bridge has occurred and, for example, mark it on a screen (for example, a 3D image of the surgical table or operating table, on which the corresponding areas are each marked with a cloud of red points). Alternatively or additionally, an acoustic alarm and/or an interruption of the HF operating device can take place simultaneously, for example.

In another embodiment, the measuring electrodes are realized in the form of an interdigital structure.

Exemplary interdigital structures can be taken from the following scientific literature, for example FIG. 2 from Tsai, Chiu, Chou (2015). *Optimal Design of SAW Gas Sensing Device by Using Improved Adaptive Neuro-Fuzzy Inference System*. IEEE Access, issue 3, p. 420-429.

Interdigital structures have finger-like structures. These structures are also referred to as interdigital electrodes and engage into each other in the manner of a comb without touching each other. The finger-like structures are made of a metal, for example.

In another embodiment, the predetermined measuring alternating voltage or the predetermined measuring alternating current has a frequency of 1 kHz to 10 kHz and/or does not correspond to a frequency by means of which the high-frequency surgery device is operated.

Thus, the measuring frequency is preferably AC and particularly preferably not a frequency component of the cutting current which is fed into the active electrode. This is advantageous for the signal-to-noise ratio and allows for a simplified, interference-free analysis or evaluation of the measuring impedance. The preferred frequency of 1 kHz to 10 kHz allows for a simplified detection of "leakages".

However, it should be mentioned that it is generally also possible to select frequencies which are at least close to the frequency of the cutting current. In this case, however, an appropriate noise filtering or synchronous demodulation (for example, as heterodyne detection and preferably as homodyne detection) should be performed by means of which measurement signal interferences are filtered out.

In another embodiment, the measuring electrodes are disposed such that they are in electroconductive contact with one or several body locations and/or clothing of the patient.

An advantage of this embodiment is that, because of the electroconductive contact, the impedance measured between the measuring electrodes already includes the electrical resistance of the one or several body locations, and thus, in the case of looming burns, e.g., when a leakage of fluids suddenly occurs during surgery, a changing conductivity of the skin can be determined indirectly via the falling impedance. Preferably, the measuring electrodes are in direct contact with the skin surface on the operating table. Alternatively, the measuring electrodes can also be in contact with clothing worn by the patient during the surgery. Such a garment, for example a surgical gown, can absorb moisture in the event of an unexpected leakage of (bodily) fluid or disinfectant, even becoming soaked, causing a sudden impedance drop.

In another embodiment, the measuring electrodes are adhesively connected to one or several body locations of the patient so as to conduct electricity.

It is an advantage of this embodiment that a direct contact between the skin surface and the measuring electrodes is thus ensured. This increases the quality of the impedance measurement because interference signals (for example because of air gaps are avoided.

In another embodiment, a number of measuring electrodes is at least larger than a number of the one or several body location(s) of the patient to be monitored.

An advantage of this embodiment is the possibility of a more exact or more precise localization, a correction of error signals and also a redundancy, for cases where several of the measuring electrodes are in poor contact with the patient.

In another embodiment, the measuring electrodes are disposed on a surface of a patient table or integrated in the surface of the patient table.

For example, the measuring electrodes can be disposed directly on the surface of the operating table or even be integrated in the surface. Alternatively, the measuring electrodes can also be integrated in a net-like cover which is pulled over the operating table before the surgery. Furthermore, it is possible that the measuring electrodes are disposed in a hose-like net cover, for example, which can be pulled over each of the breathing hoses and/or the aspirator hoses. The patient table can be an operating chair or an operating table, for example.

This embodiment is advantageous in that a direct contact between the measuring electrodes and the skin surface of the patient can be ensured.

In another embodiment, the measuring electrodes are incorporated in a removable cover of a patient table or a mat.

An advantage of this embodiment is the simple retrofit for existing systems because the operating table can simply be covered with the cover of the patient table in which the measuring electrodes or measuring sensors are disposed. In addition, the cover can be cleaned easily. For example, the cover can be made of a fabric and/or a plastic material.

The term "incorporated" means that the measuring electrodes or measuring sensors are preferably woven, sewn, bonded, glued or otherwise fastened in the cover. Preferably, the cover should be designed with the patient's comfort in mind so as to avoid bruising or pressure points, especially during operations lasting several hours.

In another embodiment, the measuring electrodes each have electroconductive threads which are preferably woven into the cover.

An advantage of this embodiment is the simplicity of its execution. For example, a fabric in which metallic threads are woven in at a distance to one another can be used as a cover, with each of the metallic threads then acting as a measuring electrode and the impedance measurement threads in each case being carried out between two threads which do not necessarily have to be adjacent.

In another embodiment, the measuring electrodes are metrologically differentially connected in series or in parallel or inductively or capacitively coupled to each other and, preferably in their entirety, serve as a dispersive electrode of the high-frequency surgery device which discharges the high-frequency electrical energy from the biological tissue.

This embodiment is advantageous in that the measuring electrodes can be connected to each other in any way, depending on the type of electrode used. Regarding the evaluation by means of the evaluation and control unit, the specific type of connection is always decisive since the calculation of the measured variables changes depending on the type of connection. Preferably, the measuring electrodes in their entirety serve as the dispersive electrode, which has the advantage of eliminating the need for an additional dispersive electrode. The high-frequency current introduced into the tissue by means of the active electrode is then discharged via the dispersive electrode in a regulated, controlled manner.

In another embodiment, impressing the predetermined measuring alternating voltage or the predetermined measuring alternating current on the measuring electrodes takes place on the basis of a four-wire measurement.

The four-wire measurement is used for the measurement of electrical resistances with a four-wire connection if line and terminal resistances can distort the measurement. In the four-wire measuring arrangement, a known electrical measuring current flows through the resistance (the tissue lying between the measuring electrodes) via two of the lines. The voltage dropping at the resistor is tapped at high impedance via two further lines and measured with a voltmeter; the resistance to be measured is calculated according to Ohm's law.

In another embodiment, the measuring electrodes are electronically connected to each other as pairs of electrodes, such that impressing the predetermined measuring alternating voltage or the predetermined measuring alternating current and the measurement of the impedance is carried out in pairs, wherein each individual measuring electrode of the measuring electrodes is dynamically pairable with any other measuring electrode of the measuring electrodes, and wherein the measurement of the impedance per pair of measuring electrodes is preferably performed successively in time or simultaneously.

This embodiment is advantageous in that the impedance can be measured in segments or in sections. Another advantage is that possible burns can be localized inexpensively. The position or positions where burns are most likely to occur can be visually illustrated and/or marked on a screen, for example.

To "save" measuring channels and/or measuring electrodes, measuring channels can be used at several locations, which are located at a distance to one another, and interconnected with other adjacent channels. Since in the event of a leakage, adjacent electrode pairs are also likely to be affected over a large area, the location of the burn can still be determined relatively accurately in this way by "striking" (i.e., measuring a sharp drop in impedance) together with adjacent electrodes. At the same time, a higher resolution is achieved than if only fewer channels were used.

In another embodiment, evaluation and control unit is configured to measure a real part and/or imaginary part of the impedance decreasing over the measuring electrodes and/or to measure an amplitude and phase of the measuring alternating voltage or the measuring alternating current.

Measuring the amplitude and phase of the measuring alternating voltage or the measuring alternating current corresponds to determining the imaginary part and the real part of the impedance.

In another embodiment, according to the second aspect, the measuring sensors are temperature sensors, preferably thermoactive elements, which are disposed in the periphery of the patient and configured to detect a temperature as the parameter. Furthermore, in this embodiment, the evaluation and control unit is configured to generate the preferred warning signal if a relative change in temperature exceeds a predetermined first threshold.

This embodiment is advantageous in that an unwanted conductivity bridge due to contact of a body part with an electroconductive material is not generated directly via an impedance measurement, which may also be subject to noise effects, but indirectly because of the temperature increase produced by the current flow across the conductivity bridge. The first threshold is, for example, a limit temperature above which burns can potentially occur.

It should be mentioned that this measurement technique assumes a certain inertia for the formation of a burn, i.e. that it takes at least a few seconds to form a burn.

By contrast, the temperature sensors to be used have as little thermal inertia as possible, which is why thermoelectric sensor types (e.g., thermocouples, positive temperature coefficient (PTC) thermistors, negative temperature coefficient (NTC) thermistors) are particularly suitable as sensor types, since in addition to low thermal inertia they are also inexpensive to manufacture and have sufficient accuracy for temperature difference measurements.

In another embodiment, the temperature sensors are disposed on several components in the periphery of the patient, such that the evaluation and control unit is configured to determine a spatial temperature distribution in the periphery of the patient.

This embodiment is advantageous in that preferably a two-dimensional, preferably spatial, temperature distribution of the operating environment can be determined at least in sections. Particularly preferably, the monitoring unit also has one or several thermally active measuring cameras, e.g., in the form of infrared cameras, by means of which the temperature distribution of the visible operating area can be determined. By superimposing the measurement results of the temperature sensors and the thermal cameras, a three-dimensional temperature distribution of the operating environment can preferably be generated. The actual center of the operation, where the cutting is performed by means of the high-frequency surgery device, is preferably excluded from the temperature distribution, since temperatures that could cause burns are produced in this area anyway.

In another embodiment, the measuring sensors are each magnetic and/or electric antennas which are each configured to detect electromagnetic measuring signals from the periphery of the patient as the parameter, the measuring signals being generated by the high-frequency energy during operation of the high-frequency surgery device. Furthermore, according to this embodiment, the evaluation and control unit is configured to calculate a spatial distribution of electric current density (i.e., of the patient and their (preferably immediate) surroundings) from the electromagnetic measuring signals by solving a mathematical inverse problem. With magnetic antennas, the detected electromagnetic measuring signals are proportional to $1/r \cdot \partial I/\partial t$; with electric antennas, the detected electromagnetic measuring signals are proportional to $1/distance \cdot \partial V/\partial t$; with r=distance, I=electric current, t=time, V=voltage.

From the measuring signals collected by means of the antennas, the spatial distribution of electric current (density) can be calculated by solving an inverse problem. The question is how the distribution of electric current density in the operating area, which is produced by the high-frequency surgery device due to the cutting current, should look like in order to generate the measuring signals detected by means of the antennas.

Preferably, the term "antennas" means, for example, magnetic antennas (for example loopstick antennas), electric antennas (for example dipole antennas, for example $\lambda/4$, $\lambda/2$, sub-$\lambda/2$ antennas and/or short antennas having expanded capacities (i.e., a virtual extension) and/or magnetic field sensors (for example Hall sensors, SQUID sensors, magnetoresistive sensors and/or fluxgate compass).

Thus, it is possible to obtain a quasi 3D tomographic image of the spatial distribution of electric current density. If a (predetermined) threshold is exceeded or if currents occur (are calculated) in areas where no currents should flow, a warning signal can be generated. For example, the warning signal can be an acoustic, optic and/or tactile signal. Alternatively or additionally, it is possible to pause or shut off the high-frequency surgery device.

Furthermore, it is advantageous if the calculated three-dimensional current density distribution is displayed as an image and preferably overlaid with images from a 3D stereo camera (e.g., from the producer Kinect, Microsoft, Intel, NDI) in such a way that this electric current density information is visualized, for example, on a partially transmissive 3D image of the patient. This visualization is possible in real time due to today's graphics processing units (GPUs) and programmable logic gates or integrated circuits (FPGAs).

Another advantage of this embodiment is that a retrofit can be realized relatively simply and inexpensively. For example, in an operating room, several electric or magnetic antennas can be mounted in the respective corners of the room. The captured measuring signals are fed to the evaluation and control unit as a whole. For example, the evaluation and control unit can be integrated in the high-frequency generator or, as a separate arithmetic unit, be disposed so as to be separate from the high-frequency generator.

The term "inverse problem" describes a mathematical problem in which the underlying cause of the effect (here: the distribution of electric current density) is inferred from an observed or intended effect (here: the measured signals of the antennas) of a system. Reference is made to Frank Natterer: *The Mathematics of Computerized Tomography. Society for Industrial and Applied Mathematics*, Philadelphia 2001. ISBN 0-89871-493-1 for further information.

It should be mentioned that the determination of the distribution of electric current density by means of solving the inverse problem is in principle also suitable for early detection, for example, when administrating a TUR. The transurethral resection of the hypertrophic prostate (TURP) and the resections in the bladder (TURB) in Urology or the transcervical resection of the endometrium in gynecology are standard procedures. By means of a (rigid) resectoscope, bladder or prostate tissue is resected transurethrally via a loop electrode using monopolar HF surgery in combination with an electrically insulating sugar solution or bipolar HF surgery in combination with an electroconductive NaCl solution. If there is insufficient rinsing, $H_2O$ molecules can dissociate to $H_2$ and $O_2$ and accumulate at the bladder roof. If resection is performed in this gas mixture, an explosion may occur. By means of the three-dimensional distribution of electric current density, an incipient dissociation can be detected as early as possible.

Furthermore, the determination of the distribution of electric current density is also advantageous for other high-frequency surgical procedures in which the surgery is performed using an endoscope.

In another embodiment, the evaluation and control unit is configured to generate the warning signal and/or switch off the high-frequency surgery device, if the electric current density of one or several predetermined spatial positions exceeds a predetermined second threshold.

This embodiment is advantageous in that the surgeon is not required to manually shut off the HF surgery device, but instead such a shut-off is automated.

In the present invention, "second threshold" means, for example, a critical electric current density in an area other than the center of the operation where no high electric current density is to be expected.

The "one or several positions" can be represented by one or several part(s) of a back of the patient, by means of which the patient lies on the surgical table, and/or one or several part(s) of a foot or any other limb of the patient, for example.

Furthermore, particularly preferred is a monitoring unit according to another aspect of the invention, wherein the monitoring unit is configured to monitor a patient during an operation of a high-frequency surgery device, wherein the high-frequency surgery device is configured to separate and/or coagulate biological tissue by means of high-frequency energy, wherein the monitoring unit has magnetic and/or electric antennas which are each configured to detect electromagnetic measuring signals from a periphery of the patient, the electromagnetic measuring signals being generated by the high-frequency energy during an operation of the high-frequency surgery device. Furthermore, the monitoring unit has an evaluation and control unit which is configured to calculate a spatial distribution of electric current density from the electromagnetic measuring signals by solving a mathematical inverse problem.

It is obvious that the features described above and those yet to be explained below can be used not only individually or in the described combinations but also in other combinations without departing from the scope of the present invention. Thus, embodiments of the first aspect of the invention can generally also be combined arbitrarily for further aspects according to the invention without departing from the scope of the present invention.

It should also be noted that the different aspects according to the invention represent at least partly complementary alternative solutions for solving the same technical problem.

In general, the monitoring unit according to the invention and the system according to the invention can be used for all medical-technical devices, methods and/or treatment techniques in which high-frequency electrical energy is applied to the patient.

Moreover, it is understood that, in principle, synergetic technical effects can also be generated and advantageously used by the use of the monitoring unit according to the first and the second aspect as well as their respective embodiments. Thus, it can be advantageous, for example, to use the impedance measurement along with the (three-dimensional) electric current density mapping by means of electric or magnetic antennas and/or with the temperature monitoring by means of a thermoelectric sensor technology, i.e., to use several monitoring units which function differently. For example, this can provide safety-related advantages (because of fail-safes through redundancies) and also metrological advantages because physically different measurement results can be combined with each other for cross-checking, which can result in an increase in the precision of the monitoring result. Furthermore, it should be mentioned that the monitoring unit according to the invention is also used in the veterinary field, i.e., with animal surgery, and that the aforementioned patient may not necessarily be a human, but also an animal.

BRIEF DESCRIPTION OF THE DRAWING FIGURES

Embodiments of the invention are shown in the drawings and are described in more detail hereinafter.

FIG. 3 shows a schematic view of an impedance curve over time;

Figure 6:
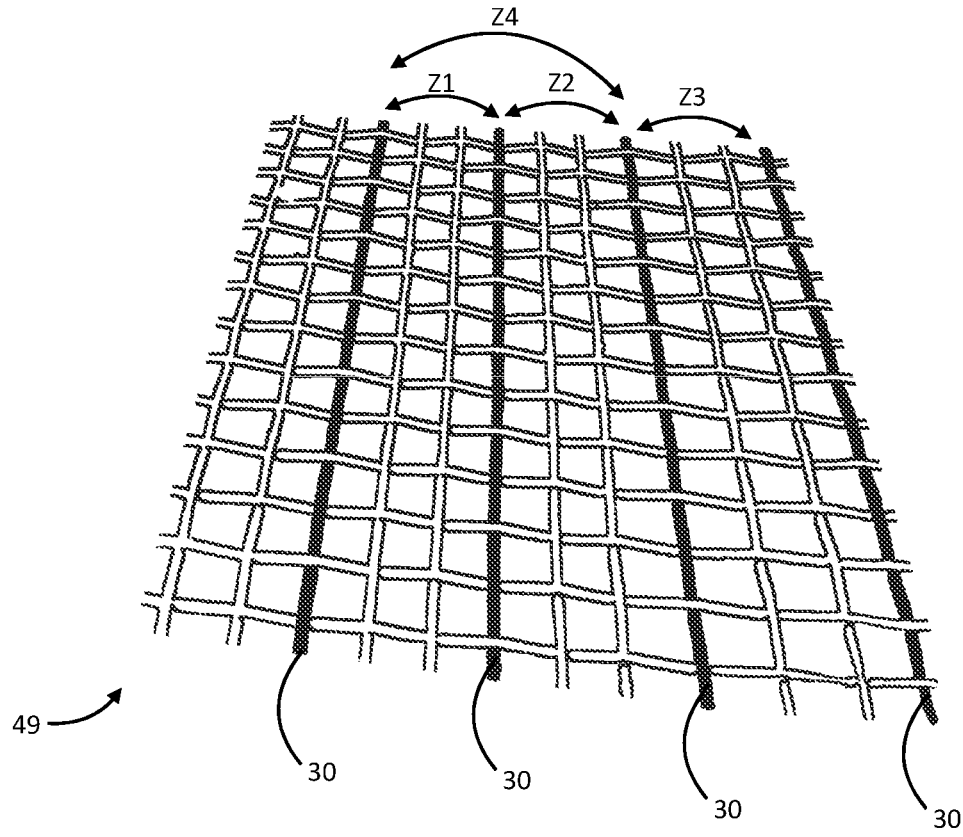
Figure 7:
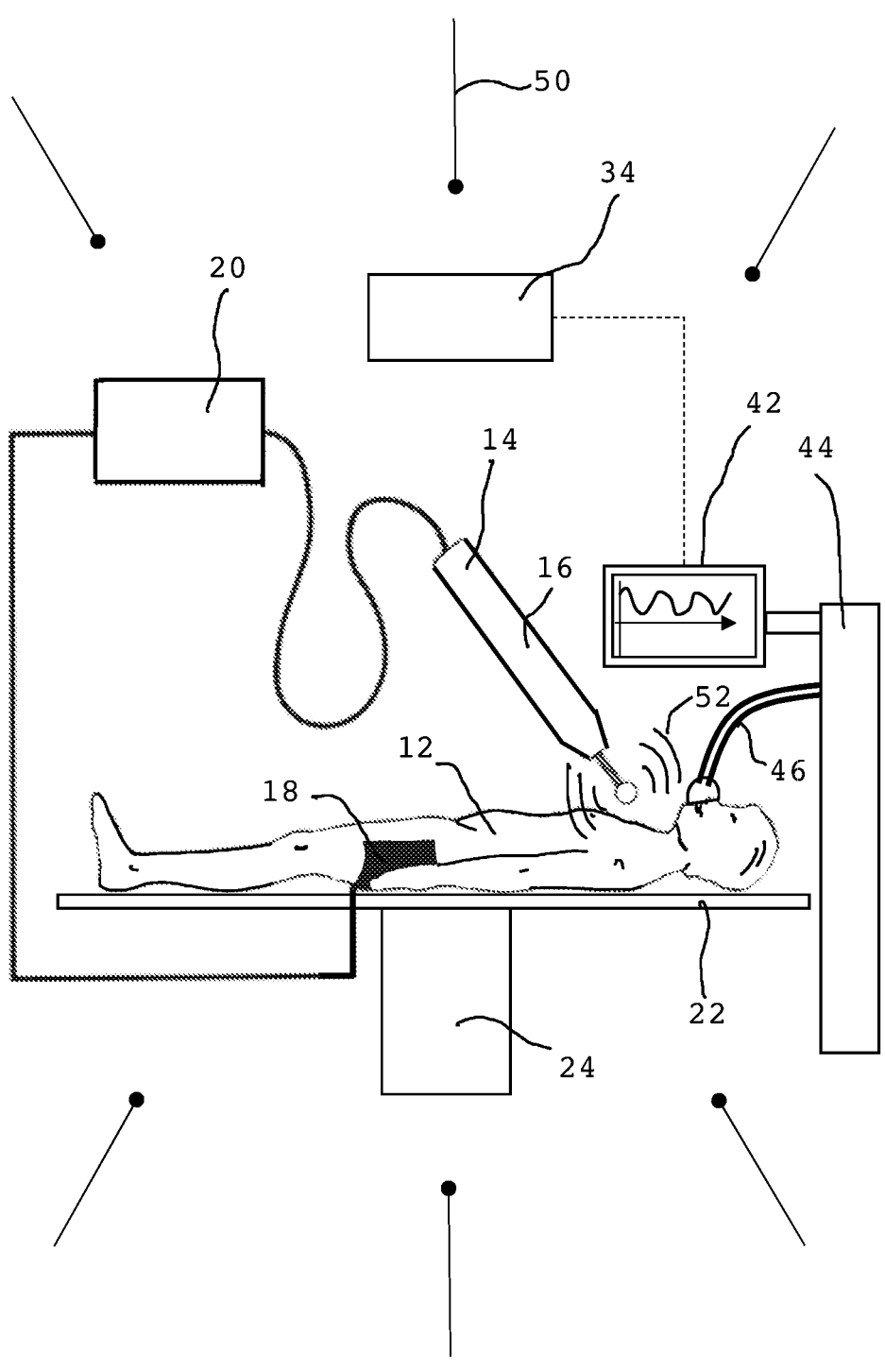

FIG. 4. shows a schematic view of an embodiment of the measuring electrodes;

FIG. 5 shows a schematic view of a second embodiment of the measuring electrodes;

FIG. 6 shows a schematic view of a third embodiment of the measuring electrodes; and FIG. 7 shows a schematic view of a third embodiment of a high-frequency surgery system according to the invention.

DETAILED DESCRIPTION

Figure 1:
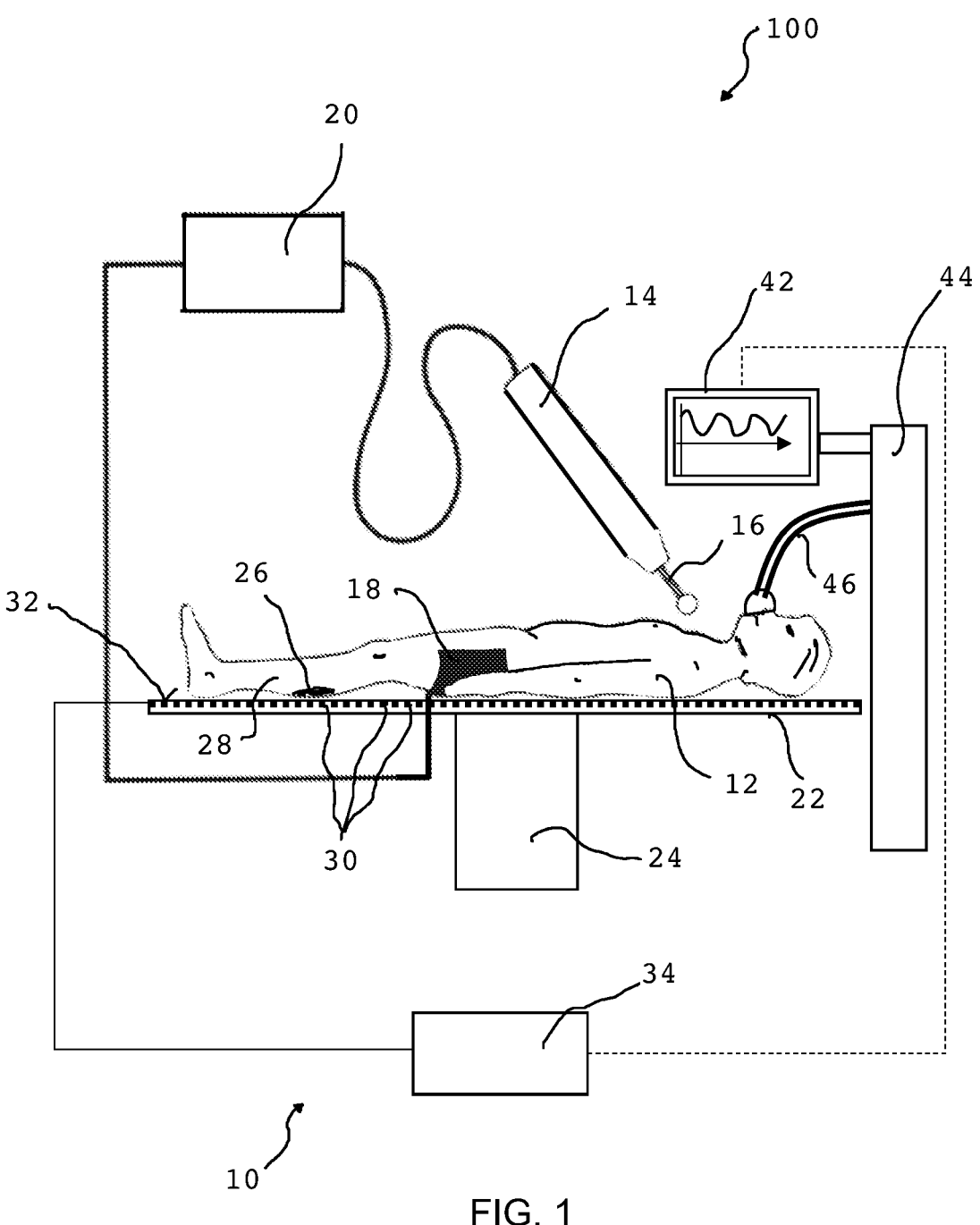
FIG. 1 shows a schematic view of a first embodiment of a high-frequency surgery system according to the invention.

FIG. 1 shows a schematic view of first embodiment of a high-frequency surgery system according to the invention. The high-frequency surgery system in its entirety is marked with reference sign 100. The high-frequency surgery system has an embodiment of a monitoring unit 10 according to the invention.

Monitoring unit 10 is configured to monitor a patient 12 during an operation of a high-frequency surgery device 14. In the present invention, high-frequency surgery device 14 is an electric scalpel with a monopolar design.

High-frequency surgery device 14 has an active electrode 16 and a dispersive electrode 18. Active electrode 16 is configured to separate and/or coagulate biological tissue of patient 12 by means of a high-frequency electrical energy or by feeding in a high-frequency alternating current. Dispersive electrode 18 is configured to discharge the high-frequency electrical energy from the biological tissue. In the present invention, dispersive electrode 18 is adhesively applied to a thigh of patient 12 as a surface electrode.

Active electrode 16 and dispersive electrode 18 are electronically coupled to a high-frequency generator 20 via one or several cable(s). High-frequency generator 20 is configured to convert an electric current from the electric grid (e.g., via a 230V, 16 A; or a 380V, 32 A connection) in a power-electronic manner (for example, by means of frequency converters) to a high-frequency alternating current required for operating the high-frequency surgery device. The frequency of this cutting current is preferably above 300 kHz and below 5 MHz. In other embodiments, dispersive electrode 18 can also be applied to other body parts of patient 12 or, alternatively, be formed by a ground connection of an operating table 22.

In the present invention, operating table 22 is a horizontal patient table which stands on a ground via a monolithic base 24. Preferably, the operating table is completely electronically insulated from an environment. In the present invention, the electric current fed from active electrode 16 into the tissue of patient 12 flows back to the grounded high-frequency generator via dispersive electrode 18 (as a mass in the electrical sense).

In the case shown in FIG. 1, however, not all the electric current injected into the patient's body by active electrode 16 flows off through the dispersive electrode because another conductivity bridge 26 is formed on a lower leg 28 of the patient, for example because of an improper handling on the part of the surgical staff when preparing the surgery or during the surgery. Conductivity bridge 26 is indicated in a simplified manner as a black spot on lower leg 28 of patient 12. An uncontrolled current flow over this conductivity bridge 26, which, in addition to dispersive electrode 18, represents an additional discharge possibility for the electric current, can cause burns in the affected areas of lower leg 28.

For a prediction or early detection of the formation of such parasitic conductivity bridges, high-frequency surgery system 100 has an embodiment of monitoring unit 10 according to the invention.

Monitoring unit 10 has measuring electrodes 30. In a simplified manner, only three of the plurality of measuring electrodes 30 are marked in the present invention. Measuring electrodes 30 are disposed in a direct periphery of patient 12 in the present invention. In this case, the peripheral arrangement of measuring electrodes 30 is limited to measuring electrodes 30 being disposed directly on a surface 32 of patient table 22. Measuring electrodes 30 are preferably each electrically insulated from one another. A drop in impedance between the measuring electrodes is caused by the current flow of the measuring alternating current through the tissue of patient 12 located between two measuring electrodes each. Measuring electrodes 30 are in direct contact with a skin of patient 12 who lies on patient table 22.

Furthermore, monitoring unit 10 has an evaluation and control unit 34. Evaluation and control unit 34 is configured to impress a predetermined measuring alternating voltage or a predetermined measuring alternating current on measuring electrodes 30. Furthermore, evaluation and control unit 34 is configured to measure, or to determine by means of current measurement or voltage measurement, an impedance Z (or an imaginary part X and/or a real part R) dropping between measuring electrodes 30. Furthermore, evaluation and control unit 34 is configured to monitor a time curve of impedance 36 (see FIG. 3) and/or a temporal change $(\partial Z/\partial t)$ thereof and to generate an acoustic, optical and/or tactile warning signal if a relative change of the impedance $(\partial Z/\partial t)$ in the time curve of the impedance 36 undercuts or exceeds a predetermined first limit value 38 and/or the impedance undercuts a predetermined second limit value 40 (cf. FIG. 3, in which time t in [s] is assigned to the abscissa, impedance Z in [Ohm] is assigned to the ordinate).

In the present invention, the warning signal is displayed on a display 42 or a display device which is connected to evaluation and control unit 34 via one or several cable(s). The display is disposed on an operation terminal 44 via which patient 12 is ventilated by means of a breathing hose 46 during the surgery.

Figure 2:
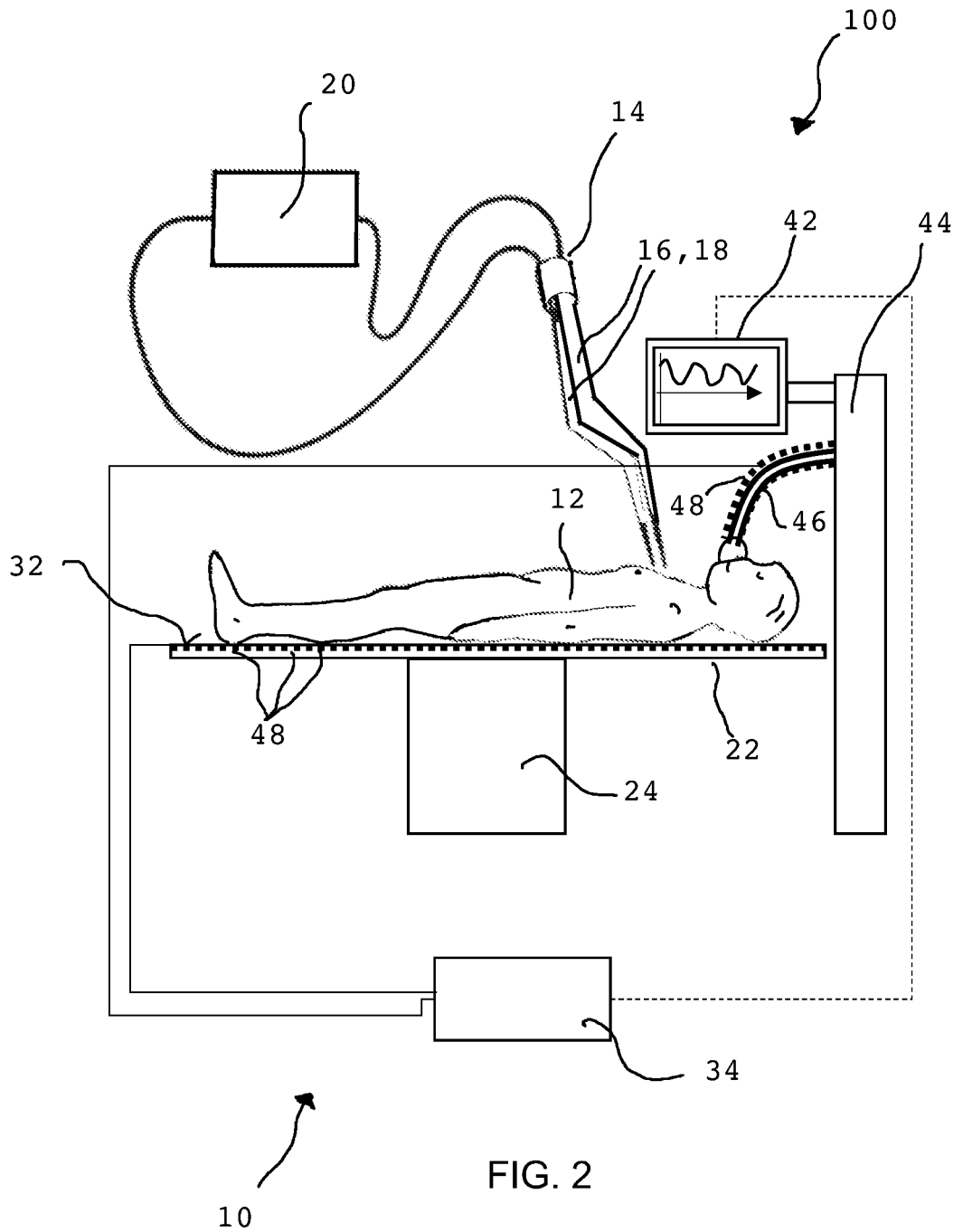
FIG. 2 shows a schematic view of a second embodiment of a high-frequency surgery system according to the invention.

FIG. 2 shows a second embodiment of high-frequency surgery system 100 with a second embodiment of monitoring unit 10. High-frequency surgery device 14 has a bipolar design of an electric scalpel in FIG. 2. With the bipolar design, active electrode 16 and dispersive electrode 18 are disposed in the manner of forceps with two branches insulated from one another, for example, wherein the active-neutral assignment can swap between the branches during operation.

Monitoring unit 10 has measuring sensors 48. Measuring sensors 48 are disposed in the periphery of patient 12. In the present invention, measuring sensors 48 are disposed over the entire surface 32 of patient table 22 so as to be at a distance to one another. Furthermore, additional measuring sensors are disposed on breathing hose 46. Measuring sensors 48 are configured to detect a parameter which is produced during the separation and/or coagulation of the biological tissue because of the high-frequency energy. Evaluation and control unit 34 is configured to generate a warning signal based on the parameter.

In the present invention, measuring sensors 48 are temperature sensors, in particular thermoelectric elements, such as thermocouples. The measured parameter is a temperature difference in Kelvin. If a parasitic current flow occurs over an additional conductivity bridge (see FIG. 1), a rise in temperature can be measured in the form of a temperature difference via temperature sensors 48. If the temperature difference measured in time exceeds a first threshold in the form of a maximum temperature $T_{Max}$, the warning signal is generated.

FIGS. 4 and 5 show two exemplary embodiments of advantageous arrangements of measuring electrodes 30. FIG. 4 shows a checkered arrangement of black and white measuring electrodes 30. The impedance can be measured between two adjacent electrodes each, but in principle also between any two pairs of positive-negative electrodes in the checkerboard arrangement, in which the measuring electrodes 30 form a pattern of spatially distributed surface electrodes, each adjacent to and preferably electrically insulated from one another. FIG. 5 shows what is known as an interdigital structure.

FIG. 6 shows an embodiment of measuring electrodes 30 which are incorporated in, e.g., woven into, a fabric in the form of metallic threads, for example. Shown fabric 49 can be made of a non-conductive cloth or polyester and have a plurality of interwoven and/or interlaced threads, for example. Some of these threads serve as measuring electrodes 30 in metallic or electrically conductive versions (e.g. carbon-based). For example, a chair or table cover for patient table 22 can be made of such a fabric. Alternatively, a (support) mat can also be made of such a fabric. Depending on how the metallic threads or measuring electrodes are woven in, a checkerboard arrangement of the electrodes can also be created.

In FIG. 6, schematic impedance measurements are marked as arrows between respective measuring electrodes 30. In the present invention, impedances $Z_1$ to $Z_4$ are measured indirectly via a current measurement or voltage measurement by evaluation and control unit 20. Impedance $Z_4$ is not measured directly between two adjacent measuring electrodes 30; instead, a measuring electrode has been skipped between measuring electrodes 30.

FIG. 7 shows a third embodiment of the high-frequency surgery system 100 with a third embodiment of monitoring unit 10. As measuring sensors 48, monitoring unit 10 has magnetic and/or electric antennas 50. Antennas 50 are each configured to detect electromagnetic signals 52 from the periphery of patient 12 as the parameter, electromagnetic signals 52 being generated by the high-frequency energy during the operation of high-frequency surgery device 14.

Evaluation and control unit 34 is configured to calculate a spatial distribution of electric current density from the electromagnetic measuring signals by solving a mathematical inverse problem; the detected measuring signals with magnetic antennas 50 being proportional to 1/distance·∂I/∂t; the detected measuring signals with electric antennas 50 being proportional to 1/distance·∂V/∂t. Antennas 50 are preferably disposed in a direct operating environment, for example on patient table 22 and/or on a ceiling over the surgical procedure and/or in corners of the operating room. In the present invention, six antennas 50 are schematically shown, of which only one has been marked for reasons of clarity.

Furthermore, a method for monitoring a patient 12 during an operation of a high-frequency surgery device 14 is particularly preferred, wherein the high-frequency surgery device 14 is configured to separate and/or coagulate biological tissue by means of high-frequency electrical energy. The method comprises the following steps: impressing a predetermined measuring alternating voltage or a predetermined measuring alternating current on measuring electrodes 30 which are disposed in a periphery of patient 12, and measuring an impedance decreasing between measuring electrodes 30, and monitoring a time curve of impedance 36 and/or a temporal change thereof.

Also preferred as an alternative solution is a method for monitoring a patient 12 during an operation of a high-frequency surgery device 14, wherein high-frequency surgery device 14 is configured to separate and/or coagulate biological tissue by means of high-frequency electrical energy. The method comprises the following steps: detecting electromagnetic measuring signals from a periphery of the patient by means of magnetic and/or electric antennas, wherein the electromagnetic measuring signals are generated by the high-frequency energy during the operation of the high-frequency surgery device; and calculating a spatial distribution of electric current density (or of the patient and their periphery) from the electromagnetic measuring signals by solving a mathematical inverse problem.

The preferred methods for monitoring a patient 12 during an operation of a high-frequency surgical device 14 can be designed in a respective method-specific variation according to the configurations and embodiments disclosed above without being mentioned here redundantly.

The invention claimed is:

1. A monitoring unit configured to monitor a patient during an operation of a high-frequency surgery device, wherein the high-frequency surgery device is configured to separate and/or coagulate biological tissue by means of high-frequency electrical energy, the monitoring unit comprising:

measuring electrodes, separate from and not a part of the high frequency surgery device, adapted to be disposed in a periphery of the patient wherein the measuring electrodes are disposed on a surface of a patient table or integrated in the surface of the patient table; and an evaluation and control unit configured to impress a predetermined measuring alternating voltage or a predetermined measuring alternating current on the measuring electrodes, and to monitor an impedance decreasing between the measuring electrodes, to monitor (a) a time curve of the impedance, (b) a temporal change thereof or (c) both the time curve of the impedance and the temporal change thereof.

2. The monitoring unit according to claim 1, wherein the evaluation and control unit is further configured to generate a warning signal if a relative change in impedance in the time curve of the impedance undercuts or exceeds a predetermined first limit value and/or the impedance undercuts a predetermined second limit value.

3. The monitoring unit according to claim 2, wherein the measuring electrodes are disposed on several components in the periphery of the patient, such that the evaluation and control unit is configured to determine a spatial impedance distribution in the periphery of the patient.

4. The monitoring unit according to claim 3, wherein the monitoring unit further has a display and wherein the evaluation and control unit is configured to display the warning signal in the form of a spatial position and location of a place in the periphery of the patient at which the first limit value is exceeded or undercut and/or the second limit value is undercut on the display.

5. The monitoring unit according to claim 4, wherein the measuring electrodes form a pattern of surface electrodes which are spatially distributed, adjacent and electrically insulated from each other and wherein the evaluation and control unit is configured to measure the impedance between each two adjacent surface electrodes.

6. The monitoring unit according to claim 5, wherein the measuring electrodes are realized in the form of an interdigital structure and wherein the predetermined measuring alternating voltage or the predetermined measuring alternating current has a frequency of 1 kHz to 10 kHz and/or does not correspond to a frequency by means of which the high-frequency surgery device is operated.

7. The monitoring unit according to claim 4, wherein the measuring electrodes are disposed such that they are in electroconductive contact with one or several body locations and/or clothing of the patient.

8. The monitoring unit according to claim 7, wherein a number of measuring electrodes is at least larger than a number of the one or several body location(s) of the patient to be monitored.

9. The monitoring unit according to claim 1, wherein the measuring electrodes are incorporated in a removable cover of a patient table.

10. The monitoring unit according to claim 9, wherein the measuring electrodes each have electroconductive threads which are woven into the cover.

11. The monitoring unit according to claim 10, wherein the measuring electrodes are metrologically differentially connected in series or in parallel or inductively or capacitively coupled to each other and, preferably in their entirety, serve as a dispersive electrode of the high-frequency surgery device which discharges the high-frequency electrical energy from the biological tissue.

12. The monitoring unit according to claim 11, wherein impressing the predetermined measuring alternating voltage or the predetermined measuring alternating current on the measuring electrodes takes place on the basis of a four-wire measurement.

13. The monitoring unit according to claim 1, wherein the measuring electrodes are electronically connected to each other as pairs of electrodes, such that impressing the predetermined measuring alternating voltage or the predetermined measuring alternating current and the measurement of the impedance is carried out in pairs, wherein each individual measuring electrode of the measuring electrodes is pairable with any other measuring electrode of the measuring electrodes, and wherein the measurement of the impedance per pair of measuring electrodes is preferably performed successively in time or simultaneously.

14. The monitoring unit according to claim 13, wherein the evaluation and control unit is configured to measure a real part and/or imaginary part of the impedance decreasing over the measuring electrodes and/or to measure an amplitude and phase of the measuring alternating voltage or the measuring alternating current.

15. A monitoring unit configured to monitor a patient during an operation of a high-frequency surgery device, wherein the high-frequency surgery device is configured to separate and/or coagulate biological tissue by means of high-frequency electrical energy, the monitoring unit comprising:

measuring electrodes, separate from and not a part of the high frequency surgery device, adapted to be disposed in a periphery of the patient; and an evaluation and control unit configured to impress a predetermined measuring alternating voltage or a predetermined measuring alternating current on the measuring electrodes, and to monitor an impedance decreasing between the measuring electrodes, to monitor (a) a time curve of the impedance, (b) a temporal change thereof or (c) both the time curve of the impedance and the temporal change thereof and wherein;

(1) the evaluation and control unit is further configured to generate a warning signal if a relative change in impedance in the time curve of the impedance undercuts or exceeds a predetermined first limit value and/or the impedance undercuts a predetermined second limit value;

(2) the measuring electrodes are disposed on several components in the periphery of the patient, such that the evaluation and control unit is configured to determine a spatial impedance distribution in the periphery of the patient; and (3) the monitoring unit further has a display and wherein the evaluation and control unit is configured to display the warning signal in the form of a spatial position and location of a place in the periphery of the patient at which the first limit value is exceeded or undercut and/or the second limit value is undercut on the display.

16. The monitoring unit according to claim 15, wherein the measuring electrodes form a pattern of surface electrodes which are spatially distributed, adjacent and electrically insulated from each other and wherein the evaluation and control unit is configured to measure the impedance between each two adjacent surface electrodes.

17. The monitoring unit according to claim 16, wherein the measuring electrodes are realized in the form of an interdigital structure and wherein the predetermined measuring alternating voltage or the predetermined measuring alternating current has a frequency of 1 kHz to 10 kHz and/or does not correspond to a frequency by means of which the high-frequency surgery device is operated.

18. The monitoring unit according to claim 15, wherein the measuring electrodes are disposed such that they are in electroconductive contact with one or several body locations and/or clothing of the patient.

19. The monitoring unit according to claim 18, wherein a number of measuring electrodes is at least larger than a number of the one or several body location(s) of the patient to be monitored.

20. The monitoring unit according to claim 15, wherein the measuring electrodes are incorporated in a removable cover of a patient table.

* * * * *